(12) United States Patent
Kehoe et al.

(10) Patent No.: US 8,906,649 B2
(45) Date of Patent: Dec. 9, 2014

(54) ANTIBODIES BINDING HUMAN COLLAGEN II

(71) Applicant: Janssen Biotech, Inc., Horsham, PA (US)

(72) Inventors: John Kehoe, Spring House, PA (US); Tatiana Ort, Spring House, PA (US); Kristen Picha, Spring House, PA (US); Mary Ryan, Spring House, PA (US); John Wheeler, Spring House, PA (US); Jennifer Lee Gardiner, Seattle, WA (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 13/760,663

(22) Filed: Feb. 6, 2013

(65) Prior Publication Data
US 2014/0220634 A1    Aug. 7, 2014

Related U.S. Application Data

(62) Division of application No. 13/245,299, filed on Sep. 26, 2011, now Pat. No. 8,394,378.

(60) Provisional application No. 61/386,796, filed on Sep. 27, 2010.

(51) Int. Cl.
| C12N 15/09 | (2006.01) |
| C12N 15/13 | (2006.01) |
| C12P 21/08 | (2006.01) |
| C07H 21/04 | (2006.01) |
| C07K 16/18 | (2006.01) |

(52) U.S. Cl.
CPC ..................................... C07K 16/18 (2013.01)
USPC .................... 435/69.5; 435/70.21; 536/23.53

(58) Field of Classification Search
CPC .... C07K 16/18; C07K 16/44; C07K 2317/24; C07K 2317/33; C07K 2317/50; C12N 2015/8518
See application file for complete search history.

(56) References Cited

U.S. PATENT DOCUMENTS

| 5,502,167 A | 3/1996 | Waldmann et al. |
| 7,067,144 B2 | 6/2006 | Demopulos et al. |
| 2003/0040044 A1 | 2/2003 | Heavner et al. |
| 2003/0059937 A1 | 3/2003 | Ruben et al. |
| 2003/0108545 A1 | 6/2003 | Rockwell et al. |
| 2004/0006215 A1 | 1/2004 | Keler et al. |
| 2004/0072164 A1 | 4/2004 | Maruyama et al. |
| 2004/0213795 A1 | 10/2004 | Collins et al. |
| 2005/0069869 A1 | 3/2005 | Ambrosino et al. |
| 2005/0153442 A1 | 7/2005 | Katz et al. |
| 2006/0083735 A1 | 4/2006 | Reiter et al. |
| 2007/0134248 A1 | 6/2007 | Denney et al. |
| 2007/0192889 A1 | 8/2007 | La Rosa et al. |
| 2008/0166352 A1 | 7/2008 | Siu et al. |
| 2010/0021477 A1 | 1/2010 | Tsui et al. |
| 2010/0080808 A1 | 4/2010 | Siebel et al. |

FOREIGN PATENT DOCUMENTS

| WO | WO 01/14558 A1 | 3/2001 |
| WO | WO2005/097073 | 10/2005 |
| WO | WO 2008/135734 A1 | 11/2008 |
| WO | WO 2010/004204 A2 | 1/2010 |

OTHER PUBLICATIONS

Eck, S. L. and Wilson, J. M.,1996, in: Goodman & Gilman's The Pharmacological Basis of Therapeutics, Ninth Edition, McGraw-Hill, New York. See Chapter 5, pp. 77-101.*
Gerwin, et al., "Intraarticular drug delivery in osteoarthritis," Advanced Drug Delivery Reviews, 58: 226-242 (2006).
Hughes, et al., "Human Sing-Chain Variable Fragment That Specifically Targets Arthritic Cartilage," Arthritis & Rheumatism, 62(4): 1007-1016 (2010).
Rosenfiuh, et al., "Biofunctional polymer nanoparticles for intra-articular targeting and retention in cartilage," Nature, 7: 248-254 (2008).
Shi, et al., "De Novo Selection of High-Affinity Antibodies from Synthetic Fab Libraries Displayed on Phage as pIX Fusion Proteins," Journal of Molecular Biology, 397: 385-396 (2010).
Xu, et al., "Two monoclonal antibodies to precisely the same epitope of type II collagen select non-crossreeactive phage clones by phage display: implications for autoimmunity and molecular mimicry," Molecular Immunology, 41: 411-419 (2004).
Uniprot A7RP29, www. Uniprot.org, retrieved Jul. 11, 2012.
Uniprot B6K3A0, www. Uniprot.org, retrieved Jul. 11, 2012.
GenBank Accession PH0961,www. Ncbi.nlm.nih, Retrieved Jul. 11, 2012.
Boiers, et al., "Collagen type II is recognized by a pathogenic antibody through germline encoded structures," European Journal of Immunology, 38: 2784-2795 (2008).

* cited by examiner

*Primary Examiner* — Xiaozhen Xie
(74) *Attorney, Agent, or Firm* — Kirk Baumeister

(57) ABSTRACT

The present invention relates to antibodies against human collagen II, polypeptides and polynucleotides encoding human collagen II antibodies or fragments thereof, and methods of making and using the foregoing.

5 Claims, 6 Drawing Sheets

Figure 2.

169 heavy chains

```
Name     FR1   |CDR1  |----FR2------|  |------CDR2-------|  |-----------------FR3----------------|  |----CDR3----|  FR4                (SEQ ID NO:)
1-69     GTFS  SYAIS  WVRQAPGQGLEWMG    GIIPIFGTANYAQKFQG    RVTITADESTSTAYMELSSLRSEIDTAVYYCAR     QLWGYYALEI++++  WGQGTLVTVSS          (2)
169_76   ----  --G--  -------------    --Y-------------    ----------------------------------    PTNVLDYxxxxxxx  -----------          (56)
169_C2   ----  -----  -------------    ----------------    ----------------------------------    HWRLN-xxxxxxxx  -----------          (57)
169_22   ----  -----  -------------    ----------------    ----------------------------------    DPN-NIV-SEYFDY  -----------          (58)
169_34   ----  -----  -------------    ----------------    ----------------------------------    EGPASWDNWALDYx  -----------          (59)
169_45   ----  -----  -------------    ----------------    ----------------------------------    R-GLFDYxxxxxxx  -----------          (60)
169_G11  ----  -----  -------------    ----------------    ----------------------------------    DGYDIVLGIFDYxx  -----------          (61)
169_64   ----  -----  -------------    ----------------    ----------------------------------    NIV-D-L-DYxxxxx  -----------         (62)
169_47   ----  -----  -------------    ----------------    ----------------------------------    TSPSFDYxxxxxxx  -----------          (63)
169_31   ----  -----  -------------    ----------------    ----------------------------------    H-YYMLDYxxxxxx  -----------          (64)
```

323 heavy chains

```
Name     |--FR1----|  |CDR1  |----FR2-------|  |------CDR2-------|  |-----------------FR3----------------|  |---CDR3----|  FR4
3-23     SCAASGFTFS  SYAMS  WVRQAPGKGLEWVS    AISGSGGSTYYADSVKG    RFTISRDNSKNTLYLQMNSLRAEDTAVYYCAK      QLWGYYALEI++  WGQGTLVTVSS   (1)
323_G9   ----------  --W-H  --------------    ----------------    ----------------------------------    Y-RWGSYGILDY  -----------   (65)
323_G1   ----------  D-W--  --------------    G-W---S---------    ----------------------------------    HWGRGGD-DYxx  -----------   (66)
323_B3   ----------  -----  --------------    --RYD-S-K-------    ----------------------------------    N-KILDYxxxxxx -----------   (67)
```

5-51 heavy chains

```
Name     |--FR1----|  |CDR1  |---F-R2------|  |-----CDR2-------|  |----------------FR3-----------------|  |---CDR3----|  FR4
5-51     SCKGSGYSFT  SYWIG  WVRQMPGKGLEWMG    IIYPGDSDTRYSPSFQG    QVTISADKSISTAVLQWSSLKASDTAMYCAR       QLWGYYALEI   WGQGTLVTVSS    (3)
551_3    ----------  -----  --------------    ----------------    ----------------------------------    G-FWFFDYxx   -----------    (68)
```

L6 light chains

```
Name     |----FR1----|  |---CDR1---|  |---FR2------|  |--CDR2--|  |----------------FR3----------------|  |--CDR3--|  FR4
L6       LSLSPGERATLSC  RASQSVSSYLA   WYQQKPGQAPRLLIY  DASNRAT    GIPARFSGSGSGTDFTLTISSLEPEDFAVYYC      QQRSNWPLT  FGQGTKVEIK       (5)
551-3    -------------  ----D-W----   --------------  -------    --------------------------------      -FDT---I-  ----------       (76)
169_45   -------------  ----D-A----   --------------  -------    --------------------------------      -YDR-----  ----------       (72)
169_31   -------------  ----ADW----   --------------  -------    --------------------------------      -YDG---I-  ----------       (75)
169_64   -------------  ----DDW----   -------Y------  -------    --------------------------------      -GDTA-I--  ----------       (73)
169_34   -------------  ----DW-----   -------Y------  -------    --------------------------------      -S-TA-I--  ----------       (71)
169_47   -------------  ----RDF----   -------G------  -------    --------------------------------      -GFH--F--  ----------       (74)
169_22   -------------  ----RDF----   --------------  -------    --------------------------------      -GSA-----  ----------       (70)
169_76   -------------  ----RKF----   --------------  -------    --------------------------------      -SN---F--  ----------       (69)
```

ANTIBODIES BINDING HUMAN COLLAGEN II

CROSS-REFERENCE TO RELATED APPLICATIONS

This application is a divisional of U.S. application Ser. No. 13/245,299, filed 26 Sep. 2011, now U.S. Pat. No. 8,394,378, which claims priority to U.S. Provisional Application No. 61/386,796, filed 27 Sep. 2010, the entire contents of which is incorporated herein by reference in its entirety.

FIELD OF THE INVENTION

The present invention relates to antibodies against human collagen II, polypeptides and polynucleotides encoding human collagen II antibodies or fragments thereof, and methods of making and using the foregoing.

BACKGROUND OF THE INVENTION

Diseases and conditions that cause the destruction of cartilage within the joints pose a significant public health concern, particularly in view of the demographics of an aging population. Multiple mechanisms are involved in the degradation of articular cartilage in arthritides such as rheumatoid arthritis (RA) and osteoarthritis (OA). RA is the most common form of inflammatory arthritis, affecting 3% of women and 1% of men. OA, a non-inflammatory arthritis, is the most common form of joint disease, and is second only to cardiovascular disease as a cause of early retirement and disability.

Most treatments for joint ailments are generally systemic. Targeting a medication locally to a joint would have several advantages: increased efficacy, reduced side effects, an improved dosing schedule, and reduced cost of goods.

Current local treatments including glucocorticoids, injectable hyaluronic acid solutions, NSAIDs or other small molecules have relatively short half lives as well as systemic distribution once injected into the joint (Gerwin, et al., Adv Drug Deliv Rev, 58:226-42, 2006; Lindenhayn et al., Eur J Clin Chem Biochem, 35:355-63, 1997). Joint retention of a therapeutic can be achieved by coupling the therapeutic to a joint targeting agent (Rothenfluh et al., Nature Materials 7:248-54, 2008; WO05/097073; U.S. Pat. No. 7,067,144). However, treatments may require intra-articular injection with delivery vehicles such as liposomes, adding a layer of complexity and possible abrasion of the articulating surface.

Thus, there is a need to develop additional vehicles for efficient delivery and subsequent retention of a therapeutic in the joint.

BRIEF DESCRIPTION OF THE DRAWINGS

FIG. 2. Sequences of the heavy chain variable regions (VH) and light chain variable regions (VL) of Fabs binding human collagen II. Residues differing from the wild type human scaffold are indicated. X denotes a deleted residue in the sequence when compared to the wild type.

SUMMARY OF THE INVENTION

Figure 1:
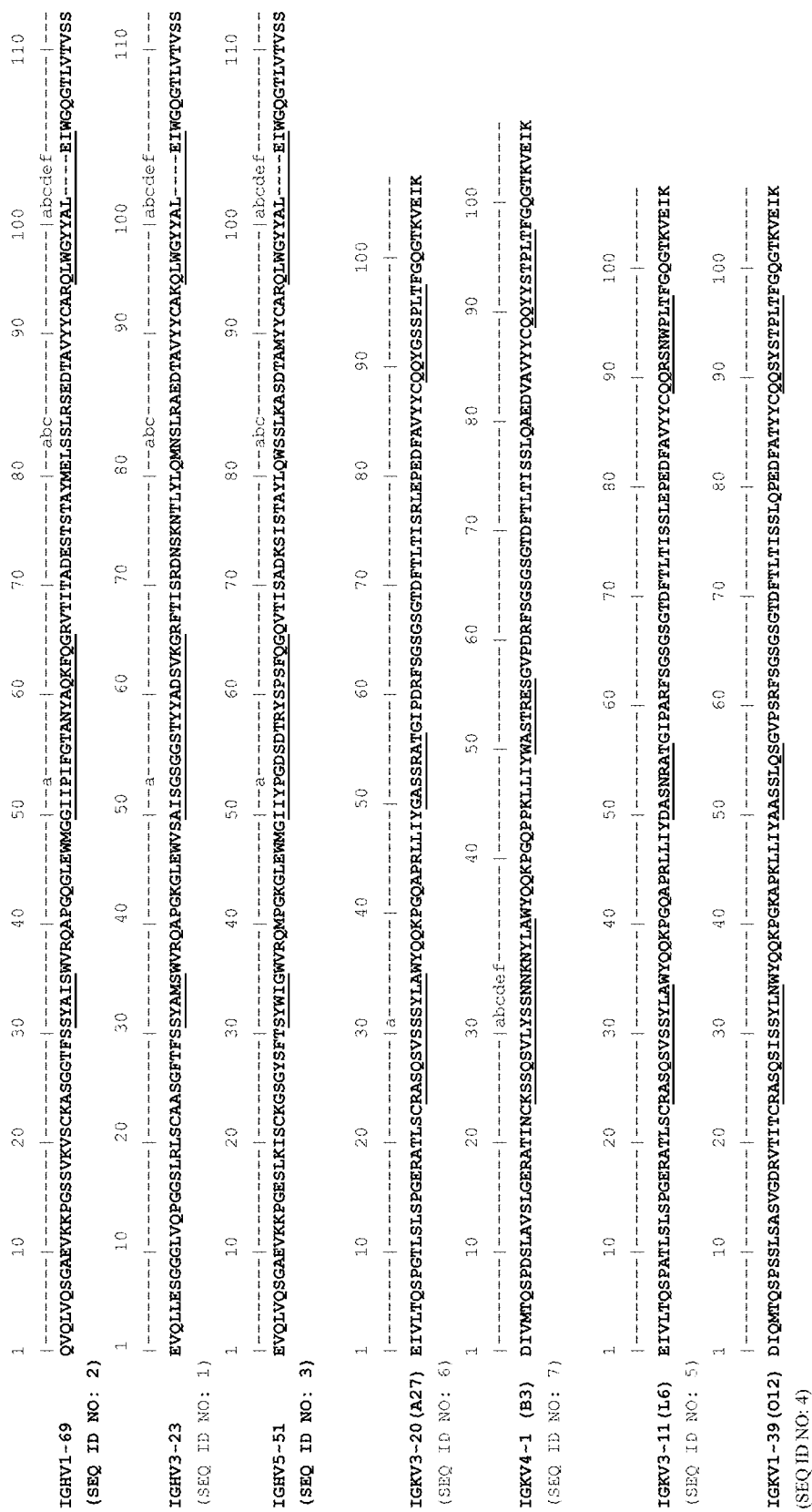
FIG. 1. Human scaffolds for the generation of de novo pIX libraries. Residue numbering according to Chothia. CDR sequences are underlined.

One aspect of the invention is an isolated monoclonal antibody or fragment thereof that binds human collagen II, comprising a heavy chain variable region (VH region) and a light chain variable region (VL region), wherein the VH region comprises the heavy chain complementarity determining region (CDR) 1, 2 and 3 (HCDR1, HCDR2, and HCDR3) sequences as shown in
  i. SEQ ID NO:s 8, 14, and 20;
  ii. SEQ ID NO:s 9, 15, and 21;
  iii. SEQ ID NO:s 9, 15, and 22;
  iv. SEQ ID NO:s 9, 15, and 23;
  v. SEQ ID NO:s 9, 15, and 24;
  vi. SEQ ID NO:s 9, 15, and 25;
  vii. SEQ ID NO:s 9, 15, and 26;
  viii. SEQ ID NO:s 9, 15, and 27;
  ix. SEQ ID NO:s 9, 15, and 28;
  x. SEQ ID NO:s 10, 16, and 29;
  xi. SEQ ID NO:s 11, 17, and 30;
  xii. SEQ ID NO:s 12, 18, and 31; or
  xiii. SEQ ID NO:s 13, 19, and 32; and
  the VL region comprises the light chain CDR 1, 2 and 3 (LCDR1, LCDR2, and LCDR3) sequences as shown in
  xiv. SEQ ID NO:s 33, 42, and 46;
  xv. SEQ ID NO:s 34, 42, and 47;
  xvi. SEQ ID NO:s 35, 43, and 48;
  xvii. SEQ ID NO:s 36, 44, and 49;
  xviii. SEQ ID NO:s 37, 42, and 50;
  xix. SEQ ID NO:s 38, 42, and 51;
  xx. SEQ ID NO:s 35, 44, and 52;
  xxi. SEQ ID NO:s 39, 42, and 53;
  xxii. SEQ ID NO:s 40, 45, and 54; or
  xxiii. SEQ ID NO:s 41, 42, and 55.

Another aspect of the invention is an isolated monoclonal antibody or fragment thereof that bind human collagen II, comprising a VH region and a VL region, wherein the VH region comprises an amino acid sequence having a sequence shown in SEQ ID NO:s 56, 57, 58, 59, 60, 61, 62, 63, 64, 65, 66, 67, or 68, and the VL region comprises an amino acid sequence having a sequence shown in SEQ ID NO:s 69, 70, 71, 72, 73, 74, 75, 76, 5, or 7.

Another aspect of the invention is an isolated antibody that binds human collagen II, comprising a VH region and a VL region, wherein the VH region comprises the HCDR1, HCDR2, and HCDR3 sequences as shown in SEQ ID NO:s 9, 15, and 28, and the VL region comprises the LCDR1, LCDR2, and LCDR3 sequences as shown in SEQ ID NO:s 39, 42, and 53.

Another aspect of the invention is an isolated monoclonal antibody or fragment thereof that binds human collagen II, comprising a VH region and a VL region, wherein the VH region comprises the HCDR1, HCDR2, and HCDR3 sequences as shown in SEQ ID NO:s 11, 17, and 30, and the VL region comprises the LCDR1, LCDR2, and LCDR3 sequences as shown in SEQ ID NO:s 34, 42, and 47.

Another aspect of the invention is an isolated antibody heavy chain variable region comprising the amino acid sequence shown in SEQ ID NO:s 56, 57, 58, 59, 60, 61, 62, 63, 64, 65, 66, 67, or 68.

Another aspect of the invention is a isolated antibody light chain variable region comprising the amino acid sequence shown in SEQ ID NO:s 69, 70, 71, 72, 73, 74, 75, or 76.

Another aspect of the invention is isolated polynucleotides encoding antibody heavy chain variable regions and antibody light chain variable regions of the invention.

Another aspect of the invention is a vector comprising at least one polynucleotide of the invention.

Another aspect of the invention is a host cell comprising the vector of the invention.

Another aspect of the invention is a method of making an antibody that binds human collagen II, comprising culturing the host cell of the invention and recovering the antibody produced by the host cell.

DETAILED DESCRIPTION OF THE INVENTION

All publications, including but not limited to patents and patent applications, cited in this specification are herein incorporated by reference as though fully set forth.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "antibody" includes whole antibodies and any fragments thereof. Antibody fragments comprise at least a portion of an immunoglobulin molecule, such as a complementarity determining region (CDR), a variable region, a constant region, or a framework region from either antibody heavy or light chain. An antibody may be a Fab, F(ab'), F(ab')$_2$, scFv, dsFv, or diabody. An antibody may be a monoclonal antibody (mAb), chimeric, humanized, or human antibody, dimeric, tetrameric or multimeric. Structures of the above mentioned antibody fragments, and techniques for the preparation and use of the antibodies and fragments thereof are well known in the art (Ausubel, et al., ed., Current Protocols in Molecular Biology, John Wiley & Sons, Inc., NY 1987-2001; Sambrook, et al., Molecular Cloning: A Laboratory Manual, 2$^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, N.Y., 1997-2001; Kohler et al., Nature, 256:495-497, 1975; Queen et al., Proc Natl Acad Sci, 86:10029-33, 1989; U.S. Pat. No. 4,816,567). For example, murine mAbs can be made by the hybridoma method of Kohler et al., Nature 256:495-497, 1975. Chimeric mAbs can be prepared by the method disclosed in U.S. Pat. No. 4,816, 567. Human-adapted mAbs having CDRs derived from a non-human donor immunoglobulin (typically murine) and the remaining immunoglobulin-derived parts of the molecule being derived from one or more human immunoglobulins can be prepared by techniques known to those skilled in the art such as that disclosed in U.S. Pat. No. 5,225,539. Human framework sequences useful for human-adaptation can be selected from relevant databases by those skilled in the art. Optionally, human-adapted mAbs can be further modified by incorporating altered framework support residues to preserve binding affinity by techniques such as those disclosed in Queen et al., Proc. Natl. Acad. Sci. (USA), 86:10029-10032, 1989 and Hodgson et al., Bio/Technology, 9:421, 1991.

Fully human mAbs lacking any non-human sequences can be prepared from human immunoglobulin transgenic mice by techniques referenced in, e.g., Lonberg et al., Nature 368: 856-859, 1994; Fishwild et al., Nature Biotechnology 14:845-851, 1996; and Mendez et al., Nature Genetics 15:146-156, 1997. Human mAbs can also be prepared and optimized from phage display libraries by techniques referenced in, e.g., Knappik et al., J. Mol. Biol. 296:57-86, 2000; and Krebs et al., J. Immunol. Meth. 254:67-84 2001). Fragments of antibodies e.g., Fab, F(ab')2, Fd, and dAb fragments may be produced by cleavage of the antibodies or by recombinant engineering. For example, Fab and F(ab')2 fragments may be generated by treating the antibodies with an enzyme such as pepsin.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

An antibody variable region consists of a "framework" region interrupted by three "antigen-binding sites". The antigen-binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat, J. Exp. Med. 132:211-250, 1970; Kabat et al., Sequences of Proteins of Immunological Interest, 5th Ed. Public Health Service, National Institutes of Health, Bethesda, Md., 1991). (ii) "Hypervariable regions", "HVR", or "HV", three in the VH (H1, H2, H3) and three in the VL (L1, L2, L3), refer to the regions of an antibody variable domains which are hypervariable in structure as defined by Chothia and Lesk (Chothia and Lesk, Mol. Biol. 196:901-917, 1987). Other terms include "IMGT-CDRs" (Lefranc et al., Dev. Comparat. Immunol. 27:55-77, 2003) and "Specificity Determining Residue Usage" (SDRU) (Almagro, Mol. Recognit. 17:132-143, 2004). The International ImMunoGeneTics (IMGT) database (http://_www_imgt_org) provides a standardized numbering and definition of antigen-binding sites. The correspondence between CDRs, HVs and IMGT delineations is described in Lefranc et al., Dev. Comparat. Immunol. 27:55-77, 2003.

"Framework" or "framework sequences" are the remaining sequences of a variable region other than those defined to be antigen-binding site. The framework is typically divided into four regions, FR1, FR2, FR3, and FR3, which form a scaffold for the three antigen-binding sites in each variable region. Because the antigen-binding site can be defined by various terms as described above, the exact amino acid sequence of a framework depends on how the antigen-binding site was defined.

The term "antibody that binds human collagen II" as used herein refers to an antibody that binds human collagen II with an EC50 of 1 μg/ml or less in an ELISA assay using plates coated with 10 μg/mL of human collagen II according to the method described in Example 2.

The term "human collagen II" or huColII as used herein refers to human type II collagen isolated from cartilage. Human collagen II is synthesized as procollagen alpha Col2A1 chains (SEQ ID NO: 79). The procollagen molecule is secreted into the extracellular matrix where it forms fibrils. Fibril formation is accompanied by the removal of the C- and N-propeptides by specific proteinases. Processing of the fibrillar hucolII is well known.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than 50 amino acids may be referred to as "peptides".

Conventional one and three-letter amino acid codes are used herein as follows:

| Amino acid | Three-letter code | One-letter code |
|---|---|---|
| Alanine | ala | A |
| Arginine | arg | R |
| Asparagine | asn | N |
| Aspartate | asp | D |
| Cysteine | cys | C |
| Glutamate | glu | E |
| Glutamine | gln | Q |
| Glycine | gly | G |
| Histidine | his | H |
| Isoleucine | ile | I |
| Leucine | leu | L |
| Lysine | lys | K |
| Methionine | met | M |
| Phenylalanine | phe | F |
| Proline | pro | P |
| Serine | ser | S |
| Threonine | thr | T |
| Tryptophan | trp | W |
| Tyrosine | tyr | Y |
| Valine | val | V |

Compositions of Matter

The present invention provides monoclonal antibodies that bind human collagen II. These antibodies are useful as research reagents, diagnostic reagents, and vehicles for delivering a therapeutic agent for example to a joint.

The invention provides novel antigen-binding sites and immunoglobulin chains derived from human immunoglobulin gene libraries.

One embodiment of the invention is an isolated monoclonal antibody or fragment thereof that binds human collagen II, comprising a heavy chain variable region (VH region) and a light chain variable region (VL region), wherein the VH region comprises the heavy chain complementarity determining region (CDR) 1, 2 and 3 (HCDR1, HCDR2, and HCDR3) sequences and the VL region comprises the light chain complementarity determining region (CDR) 1, 2 and 3 (LCDR1, LCDR2, and LCDR3) sequences as shown Table 1.

TABLE 1

| | | | SEQ ID NO: | | | | | | | | |
|---|---|---|---|---|---|---|---|---|---|---|---|
| Fab ID | VH ID | VL ID | HCDR1 | HCDR2 | HCDR3 | LCDR1 | LCDR2 | LCDR3 | VH | VL |
| Fab 169-76 | VH169-76 | VL169-76 | 8 | 14 | 20 | 33 | 42 | 46 | 56 | 69 |
| Fab169-C2 | VH169-C2 | VLL6 | 9 | 15 | 21 | 34 | 42 | 47 | 57 | 5 |
| Fab169-22 | VH169-22 | VL169-22 | 9 | 15 | 22 | 35 | 43 | 48 | 58 | 70 |
| Fab169-34 | VH169-34 | VL169-34 | 9 | 15 | 23 | 36 | 44 | 49 | 59 | 71 |
| Fab169-45 | VH169-45 | VL169-45 | 9 | 15 | 24 | 37 | 42 | 50 | 60 | 72 |
| Fab169-G11 | VH169-G11 | VLL6 | 9 | 15 | 25 | 34 | 42 | 47 | 61 | 5 |
| Fab169-64 | VH169-64 | VL169-64 | 9 | 15 | 26 | 38 | 42 | 51 | 62 | 73 |
| Fab169-47 | VH169-47 | VL169-47 | 9 | 15 | 27 | 35 | 44 | 52 | 63 | 74 |
| Fab169-31 | VH169-31 | VL169-31 | 9 | 15 | 28 | 39 | 42 | 53 | 64 | 75 |
| Fab323-G9 | VH323-G9 | VLB3 | 10 | 16 | 29 | 40 | 45 | 54 | 65 | 7 |
| Fab323-G1 | VH323-G1 | VLL6 | 11 | 17 | 30 | 34 | 42 | 47 | 66 | 5 |
| Fab323-B3 | VH323-B3 | VLB3 | 12 | 18 | 31 | 40 | 45 | 54 | 67 | 7 |
| Fab551-3 | VH551-3 | VL551-3 | 13 | 19 | 32 | 41 | 42 | 55 | 68 | 76 |

Antibodies having conservative substitutions in the heavy and light chain sequences shown in Table 1 (SEQ ID NO:s 8-76) are encompassed within the scope of the invention. The conservative substitution may reside in the framework regions, or in antigen-binding sites, as long they do not adversely affect the properties of the antibody. Substitutions may be made to improve antibody properties, for example stability or affinity. Conservative substitutions will produce molecules having functional and chemical characteristics similar to those molecules into which such modifications are made. Exemplary amino acid substitutions are shown in Table 2. Furthermore, any native residue in the polypeptide may also be substituted with alanine, as has been previously described for alanine scanning mutagenesis (MacLennan et al., Acta Physiol. Scand. Suppl. 643:55-67, 1998; Sasaki et al., Adv. Biophys. 35:1-24, 1998) Amino acid substitutions can be done for example by PCR mutagenesis (U.S. Pat. No. 4,683,195). Libraries of variants can be generated using well known methods, for example using random (NNK) or non-random codons, for example DVK codons, which encode 11 amino acids (ACDEGKNRSYW) (SEQ ID NO:80). The resulting variants can be characterized for their binding to human collagen II as described in Examples, or for other properties such as stability using well known methods.

TABLE 2

| Original residue | Exemplary substitutions |
|---|---|
| Ala (A) | Val, Leu, Ile |
| Arg (R) | Lys, Gln, Asn |
| Asn (N) | Gln |
| Asp (D) | Glu |
| Cys (C) | Ser, Ala |

TABLE 2-continued

| Original residue | Exemplary substitutions |
|---|---|
| Gln (Q) | Asn |
| Gly (G) | Pro, Ala |
| His (H) | Asn, Gln, Lys, Arg |
| Ile (I) | Leu, Val, Met, Ala, Phe |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala, Tyr |
| Pro (P) | Ala |
| Ser (S) | Thr, Ala, Cys |
| Thr (T) | Ser |
| Trp (W) | Tyr, Phe |
| Tyr (Y) | Trp, Phe, Thr, Ser |
| Val (V) | Ile, Met, Leu, Phe, Ala |

In other embodiments, the invention provides an isolated monoclonal antibody or fragment thereof that bind human collagen II, comprising a VH region and a VL region, wherein the VH region comprises an amino acid sequence having a sequence shown in SEQ ID NO:s 56, 57, 58, 59, 60, 61, 62, 63, 64, 65, 66, 67, or 68, and the VL region comprises an amino acid sequence having a sequence shown in SEQ ID NO:s 69, 70, 71, 72, 73, 74, 75, 76, 5, or 7.

Although the embodiments illustrated in the Examples comprise pairs of variable regions, one from a heavy and one from a light chain, a skilled artisan will recognize that alternative embodiments may comprise single heavy or light chain variable regions. The single variable region can be used to screen for a second variable region capable of forming a two-domain specific antigen-binding fragment capable of, for example, binding to human collagen II. The screening may be accomplished by phage display screening methods using for example hierarchical dual combinatorial approach disclosed in Intl. Publ. No. WO92/01047. In this approach, an individual colony containing either a H or L chain clone is used to infect a complete library of clones encoding the other chain (L or H), and the resulting two-chain specific antigen-binding domain is selected in accordance with phage display techniques as described.

In another aspect, the invention provides isolated antibody heavy chains and light chains comprising the amino acid sequences shown in SEQ ID NO:s 56, 57, 58, 59, 60, 61, 62, 63, 64, 65, 66, 67, or 68 for heavy chains and SEQ ID NO:s 69, 70, 71, 72, 73, 74, 75, 76, 77, 78, and 79 for light chains.

Another aspect of the invention is isolated polynucleotides encoding any of the antibodies of the invention or their complement. Certain exemplary polynucleotides are disclosed herein, however, other polynucleotides which, given the degeneracy of the genetic code or codon preferences in a given expression system, encode the antibodies of the invention are also within the scope of the invention. Polynucleotides encoding antibodies of the invention are prepared by well known methods. These methods include, but are not limited to, isolation from a natural source (in the case of naturally occurring amino acid sequence variants) or preparation by oligonucleotide-mediated (or site-directed) mutagenesis, PCR mutagenesis, and chemical gene synthesis.

Exemplary antibodies of the invention may be of the IgG, IgD, IgE, IgA or IgM isotypes. Additionally, the antibodies of the invention can be post-translationally modified by processes such as glycosylation, isomerization, deglycosylation or non-naturally occurring covalent modification such as the addition of polyethylene glycol (PEG) moieties (pegylation) and lipidation. Such modifications may occur in vivo or in vitro. For example, the antibodies of the invention can be conjugated to polyethylene glycol (PEGylated) to improve their pharmacokinetic profiles. Conjugation can be carried out by techniques known to those skilled in the art. Conjugation of therapeutic antibodies with PEG has been shown to enhance pharmacodynamics while not interfering with function. (Deckert et al., Int. J. Cancer 87:382-390, 2000; Knight et al., Platelets 15:409-418, 2004; Leong et al., Cytokine 16:106-119, 2001; Yang et al., Protein Eng. 16:761-770, 2003).

Pharmacokinetic properties of the antibodies of the invention can be enhanced through Fc modifications by techniques known to those skilled in the art. The "Fc" of an antibody is not involved directly in binding of an antibody to an antigen, but exhibits various effector functions. An antibody "Fc" is a term well known and is defined on the basis of papain cleavage of antibodies. The Fc of an antibody is directly involved in ADCC (antibody-dependent cell-mediated cytotoxicity) and CDC (complement-dependent cytotoxicity) based on complement activation, C1q binding and Fc receptor binding. Complement activation (CDC) is initiated by binding of complement factor C1q to the Fc of most IgG antibody subclasses. While the influence of an antibody on the complement system is dependent on certain conditions, binding to C1q is caused by defined binding sites in the Fc. Such binding sites are known in the state of the art and described by, e.g., Boakle et al., Nature 282: 742-43, 1979; Lukas et al., J. Immunol. 127: 2555-60, 1981; Brunhouse and Cebra, Mol. Immunol. 16: 907-17, 1979; Burton et al., *Nature* 288:338-44, 1980; Thommesen et al., Mol. Immunol. 37: 995-1004, 2000; Idusogie et al., J. Immunol. 164:4178-84, 2000; Hezareh et al., J. Virology 75:12161-68, 2001; Morgan et al., Immunology 86:319-24, 1995; EP 0307434. Such binding sites are, e.g., L234, L235, D270, N297, E318, K320, K322, P331, and P329 (numbering according to EU index of Kabat). Antibodies of subclass IgG1, IgG2 and IgG3 usually show complement activation and C1q binding, whereas IgG4 does not activate the complement system and does not bind C1q.

The antibodies of the invention are characterized in that the constant chains are of human origin. Such constant chains are well known and described, e.g., by Kabat (see e.g. Johnson and Wu, Nuc Acids Res. 28, 214-18, 2000). For example, a useful human heavy chain constant region comprises SEQ ID NO: 77. For example, a useful human light chain constant region comprises an amino acid sequence of a kappa-light chain constant region of SEQ ID NO: 78.

The antibodies of the invention may bind human collagen II with a $K_d$ less than or equal to about $10^{-6}$, $10^{-7}$, $10^{-8}$, $10^{-9}$, $10^{-10}$, $10^{-11}$ or $10^{-12}$ M. The affinity of an antibody to human collagen II can be determined experimentally using any suitable method. Such methods may utilize Biacore or KinExA instrumentation, ELISA or competitive binding assays known to those skilled in the art.

Another embodiment of the invention is a vector comprising at least one polynucleotide of the invention. The heavy and light chain variable domains of the invention are combined with sequences of promoter, translation initiation, constant region, 3' untranslated region, polyadenylation, and transcription termination to form expression vector constructs. The heavy and light chain expression constructs can be combined into a single vector, co-transfected, serially transfected, or separately transfected into host cells which are then fused to form a single host cell expressing both chains.

Another embodiment of the invention is a host cell comprising a vector of the invention. Such host cells may be eukaryotic cells, bacterial cells, plant cells or archeal cells. Exemplary eukaryotic cells may be of mammalian, insect, avian or other animal origins. Mammalian eukaryotic cells include immortalized cell lines such as hybridomas or myeloma cell lines such as SP2/0 (American Type Culture Collection (ATCC), Manassas, Va., CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATTC CRL-TIB-196). Other useful cell lines include those derived from Chinese Hamster Ovary (CHO) cells such as CHO-K1SV (Lonza Biologics, Walkersville, Md.), CHO-K1 (ATCC CRL-61) or DG44.

Another embodiment of the invention is a method of making an antibody binding human collagen II comprising culturing a host cell of the invention and recovering the antibody produced by the host cell. Methods of making antibodies and purifying them are well known in the art.

USES OF THE INVENTION

The antibodies of the invention are useful as research agents, and as delivery agents of therapeutic molecules to sites expressing human collagen II, such as a joint.

Arthritis, including osteoarthritis, rheumatoid arthritis, arthritic joints as a result of injury, and the like, are common inflammatory conditions which would benefit from the local delivery and joint retention of anti-inflammatory proteins and therapeutic molecules.

Therapeutic molecules may be coupled to the antibodies of the invention for improved joint retention. Therapeutic molecules may be proteins or chemical compounds. Exemplary therapeutic molecules are growth factors, cytokines and anti-inflammatory agents, proteins that induce growth and repair of collagen, as well as small molecules inhibiting proteolytic destruction of joint tissue. Therapeutic proteins may be coupled to the anti-collagen antibodies of the invention or fragments thereof by generating fusion proteins using well known recombinant methods. For example, the N-terminus of the therapeutic protein may be directly linked to the C-terminus of an antibody of the invention via an amide bond or a peptide linker. Exemplary fusion constructs are described in e.g. U.S. Pat. No. 5,116,964, U.S. Pat. No. 5,709,859, Intl. Publ. Nos. WO04/002417 and WO05/081687. Therapeutic molecules may also be coupled to the antibodies of the invention using chemical crosslinking well known in the art, for example using hydrazone or semicarbazone linkage.

The antibodies of the invention with optionally coupled therapeutic molecule may be prepared as pharmaceutical compositions containing an effective amount of the therapeutic molecule as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Methods for preparing parenterally administrable compositions are well known and are described in more detail in, for example, "Remington's Pharmaceutical Science", 15th ed., Mack Publishing Company, Easton, Pa.

The antibodies of the invention can be lyophilized for storage and reconstituted in a suitable carrier prior to use. This technique has been shown to be effective with conventional immunoglobulins and protein preparations and art-known lyophilization and reconstitution techniques can be employed.

The present invention will now be described with reference to the following specific, non-limiting examples.

EXAMPLE 1

Identification of Collagen II Binding mAbs

Human collagen II-binding Fabs were selected from de novo pIX phage display libraries (Shi et al., J. Mol. Biol. 397:385-396, 2010; WO2009085462A1; U.S. Pat. Appl. No. US20100021477). The libraries were generated by diversifying human germline VH genes IGHV1-69*01, IGHV3-23*01, and IGHV5-51*01, and human germline VLkappa genes O12 (IGKV1-39*01), L6 (IGKV3-11*01), A27 (IGKV3-20*01), and B3 (IGKV4-1*01). To assemble complete VH and VL domains, the IGHV genes were recombined with the human IGHJ-4 minigene via the H3 loop, and the IGKV genes were recombined with the IGKJ-1 minigene. The positions in the heavy and light chain variable regions around H1, H2, L1, L2 and L3 loops corresponding to positions identified to be frequently in contact with protein and peptide antigens were chosen for diversification. Sequence diversity at selected positions was limited to residues occurring at each position in the IGHV or IGLV germline gene families of the respective IGHV or IGLV genes. Diversity at the H3 loop was generated by utilizing short to mid-sized synthetic loops of lengths 7-14 amino acids. The amino acid distribution at H3 was designed to mimic the observed variation of amino acids in human antibodies. Library design is detailed in Shi et al., J. Mol. Biol. 397:385-396, 2010. Diversity in the generated libraries for VH H1 and H2 is shown in Table 4, for H3 in Table 4, and for VL L1, L2 and L3 in Table 5. The scaffolds utilized to generate libraries were named according to their human VH and VL germline gene origin. Sequences of the constructed VH and VL scaffolds used for diversification are shown in SEQ ID NO:s 1-7. (3-23: SEQ ID NO: 1; 1-69: SEQ ID NO: 2; 5-51: SEQ ID NO: 3; 012: SEQ ID NO: 4; L6: SEQ ID NO: 5; L27: SEQ ID NO: 6; B3: SEQ ID NO: 7) (FIG. 1). The three heavy chain libraries were combined with the four germline light chains or germline light chain libraries to generate 24 unique VH:VL combinations for screening.

TABLE 3

| Loop | Position* | Scaffold | | |
|------|-----------|------|------|------|
| | | 3-23 | 1-69 | 5-51 |
| H1 | 31 | SDNT | S | SNT |
| | 32 | Y | Y | Y |
| | 33 | AGW | AG | W |
| | 34 | M | I | I |
| | 35 | SH | S | SG |

TABLE 3-continued

| Loop | Position* | Scaffold | | |
|------|-----------|----------|----|----|
|      |           | 3-23     | 1-69 | 5-51 |
| H2   | 50        | VANG     | GW   | IR   |
|      | 51        | I        | I    | I    |
|      | 52        | SNKW     | IS   | YD   |
|      | 52a       | YSGQ     | PA   | P    |
|      | 53        | SD       | IY   | GS   |
|      | 54        | G        | FN   | D    |
|      | 55        | SG       | G    | S    |
|      | 56        | S        | T    | DY   |

*Residue numbering according to Kabat

The libraries were panned using purified human collagen II (Chondrex, #2015, treated with 3 M guanidine, DEAE-cellulose and $Na_2HPO$, 0.5 mg/mL solution in 0.05 M acetic acid) coated on a Maxisorp plate (Nunc) at 10 µg/mL in 1× collagen dilution buffer (Chondrex). The libraries were blocked for one hour at room temperature with 3% milk in TBST. 100 µl of each library was combined by heavy chain to generate the 6 HV:HL library pairs, and applied to pre-blocked (1 hour in 3% milk in TBST) human collagen II coated plates. After 1 h incubation, the wells were washed in TBST and in PBS five times in each. 200 µL of MC1061 F' cells ($OD_{600}$~1.0) were added onto the wells for 30 minutes at 37° C., after which the infected cells were plated on 2×YT (Carb/Glu) plates and

TABLE 4

| H3 length | Codon Configuration[2] |
|-----------|------------------------|
| 7         | A, (NNS) × 3, F/L, D, Y |
| 8         | A, (NNS) × 4, F/L, D, Y |
| 9         | A, B × 5, F/L, D, Y    |
| 10        | A, B × 6, F/L, D, Y    |
| 11        | A, B × 6, (B + BY) × 1, F/L, D, Y |
| 12        | A, B × 4, (B + BY) × 4, F/L, D, Y |
| 13        | A, B × 6, (B + BY) × 3, F/L, D, Y |
| 14        | A, B × 6, (B + BY) × 4, F/L, D, Y |

Numbering according to Kabat and co-workers.
[2]Codon base compositions [A-C-G-T]
A: position 1 = [15-15-68-2] position 2 = [43-11-33-13] position 3 = [2-29-24-45]
B: position 1 = [19-14-41-26] position 2 = [28-25-33-14] position 3 = [0-34-36-30]
B + BY: Mixed primer set at this position. BY contains a tyrosine codon (TAT) sequentially replacing the B codon in these positions and is mixed at a ratio of 1:7 with a primer containing the B codon. Therefore, for CDR length 11 with one (B + BY) codon, two primers were used. One had the TAT codon at this position and the second had the B codon and these were mixed at a ratio of 1:7. For CDR length 13, the three (B + BY) codons required 4 primers, one with the B codon and three with the TAT codon in each of three positions and the B codon in the remaining 2 positions. In this case, the TAT primers were mixed at a ratio of 1:1:1:7 with the full B codon primer. Similarly, CDR-12 and CDR-14 were prepared with 5 primers.

placed at 37° C. overnight. The colonies that had grown overnight were scraped off the plates in 2 mL per plate of 2×YT (Carb/Glu/20% glycerol). 50 ml of re-suspended bacteria was used to inoculate a 20 mL culture in 2×YT (Carb) and the remainder of the bacteria were frozen. The cultures were grown at 37° C. to an $OD_{600}$ 0.5-1.0, after which 1 mL of helper phage VCSM13 (Stratagene, Cat. No. 200251) was added to the culture at a multiplicity of infection of approximately 10:1 and incubation was carried out for 30 minutes at 37° C. without shaking. Kanamycin and IPTG were added the culture and it was grown at 30° C. overnight. Phage was precipitated with 2% PEG/0.25M NaCl and re-suspended in 1 ml of PBS. One fifth of the PEG-precipitated phage was used to initiate the next round of panning and the remaining phage were stored at −20° C.

The selection cycle was repeated four times. After the last selection cycle, the colonies were scraped off in 2 mL 2×YT Carb/Glu/20% glycerol and 100 µL of the cell suspension was used to isolate plasmid DNA. The pIX was excised by Nhe1/Spe1 digestion and self-ligation of the isolated DNA. After ligation, the DNA was electroporated into electrocompetent MC1061 F' cells and plated for single colonies on 2×YT Carb/Glu.

TABLE 5

| Loop | Posi-tion* | Scaffold | | | |
|------|-----------|----------|------|------|------|
|      |           | O12      | L6   | A27  | B3   |
| L1   | 30        | SRNAD    | SRNAD | SRNTD | L    |
|      | 30a       | —        | —    | SNR  | YSHFA |
|      | 30e       | —        | —    | —    | KTNE |
|      | 31        | SNKDG    | NSKD | SNRADH | K   |
|      | 32        | YHNDWFSA | YWDFHSAN | YFHQSEK | YFHNWDAS |
| L2   | 50        | FYTNKADG | ADKGYFTN | ADGS | WSRDYA |
| L3   | 91        | SAYHPD   | RYSGF | YSHA | YSHA |
|      | 92        | FIYHNDKGR | RHNSL | YNDSHIFKG | YNDSHIFKG |
|      | 93        | STHNDRG  | NDKR | SNTDGHR | SNTDGHR |
|      | 94        | TYLVFSRGP | WA   | TYLVFAS | TYLVFAS |
|      | 96        | LWRFYIN  | WYFLIR | WYFLIR | WYFLIR |

*Residue numbering according to Kabat

EXAMPLE 2

Cross-Reactivity of Col II mAbs with Other Collagens

The human collagen II binding Fabs obtained from the initial panning were screened for cross-reactivity with human collagens I, IV and V, and rat collagens I and II.

Preparation of Fab Lysates.

Colonies were picked from the pIX-excised transformations and grown in 2×YT Carb. The next day, 50 µL of the saturated cultures were used to inoculate an expression plate containing 400 µL per well of 2×YT Carb and the plate was grown at 37° C. for 6 hours. Fab expression was induced with the addition of 1 mM IPTG and the plate was placed at 30° C. overnight. The next day, the induced Fab cultures were spun at 2000 rpm for 10 minutes, and the cleared lysate was used in subsequent assays.

ELISA

Figure 3:
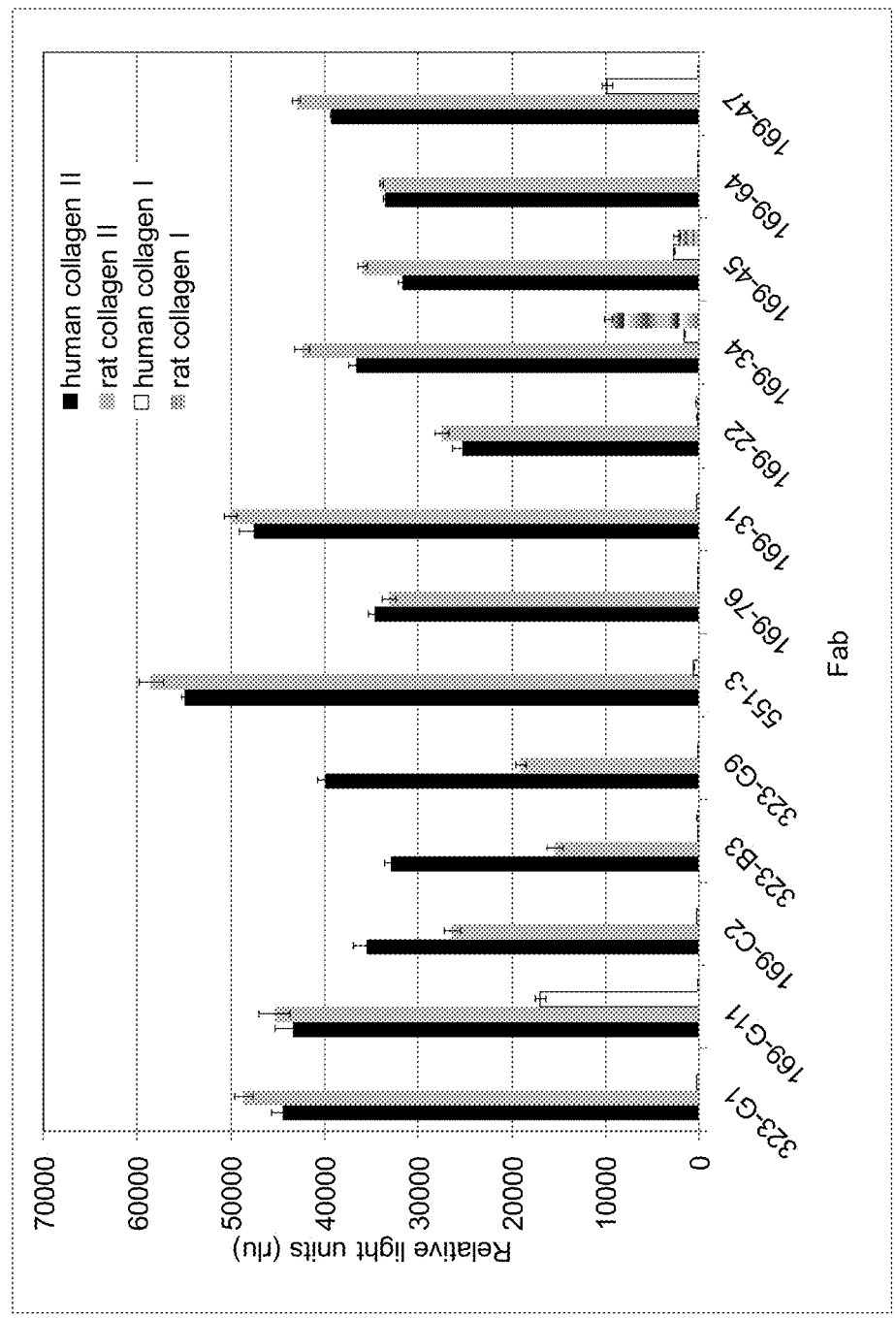
FIG. 3. Cross-reactivity of Fabs against human and rat collagens I and II.

Maxisorp ELISA plates (Nunc) were coated with 10 µg/ml human collagen I (Chondrex), human collagen II (Chondrex), rat collagen I (Chondrex), rat collagen II (Chondrex) or with 5 µg/ml human collagen IV (Chemicon) or human collagen V (Chemicon), or with anti-Fd (the Binding Site) at 1 µg/ml, all in PBS, according to manufacturer's instructions. The wells were washed three times in TBST and blocked for one hour with 200 µL 3% milk in TBST. 100 µL of the Fab lysate was added onto the wells of the coated ELISA plates, and incubated 1 hour at room temperature. The wells were washed three times followed by addition of 100 µL of anti-kappa-HRP (Southern Biotech) at 1:5000 in PBS. The plates were incubated at room temperature for one hour, washed three times with TBST, and developed with BM Chemiluminescence ELISA Substrate (Roche Applied Science). The clones that bound to human and rat collagen II without binding to human collagen I, IV or V, or rat collagen I were sequenced and unique clones were further characterized. FIG. 3 shows the ELISA data for the 13 clones chosen for further characterization. The sequences of the Fabs are shown in FIG. 2 and Table 1.

EXAMPLE 3

Col II mAbs Bind to Human Cartilage

Small-Scale Fab Purification

The Fab expression in *Escherichia coli* in 2×YT Carb (except that TurboBroth (Athena ES) was used for expression of Fab 551-3) was induced with 1 mM IPTG at 30° C. overnight. Induced bacteria were pelleted 30 min 4500 rpm, the cell pellets resuspended in lysis buffer (20 mM Tris, pH 8.5, 350 mM NaCl, 7.5 mM imidazole) with protease inhibitors, and ruptured with two passes through a microfluidizer. The cell lysate was clarified with two spins at 10,000 rpm for 10 minutes. Talon resin (Clontech) was equilibrated with lysis buffer and two mLs were added to the clarified lysate. Bound Fabs were eluted with two incubations of 5 minutes each using elution buffer (150 mM EDTA, 20 mM Tris, pH 8.5) and dialyzed in 20 mM Tris, pH 8.5. The dialyzed Fabs were further purified using a Q-sepharose Fast Flow resin (QFF resin; GE Healthcare), and used for experiments.

Cartilage-Binding Assay

Figure 4:
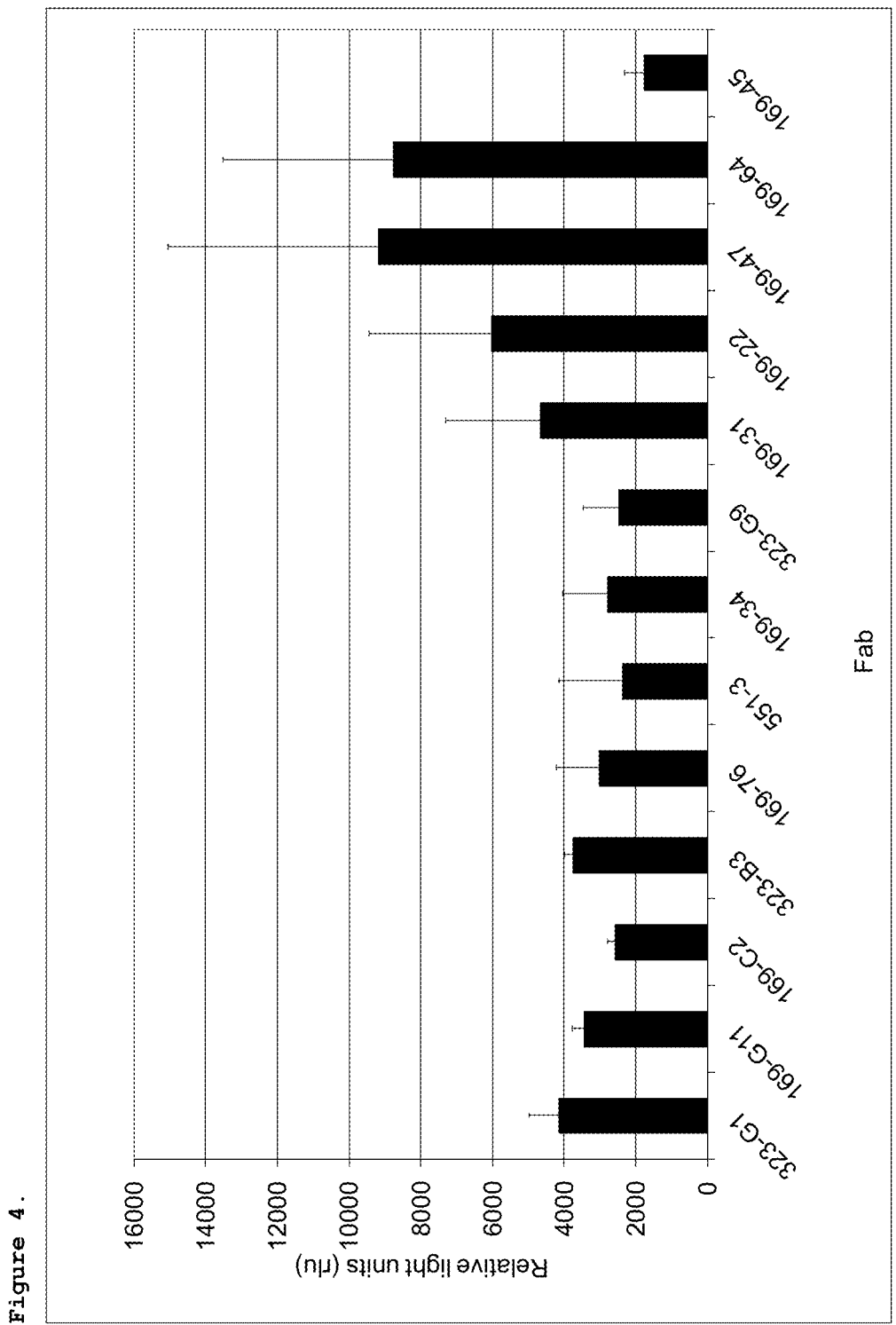
FIG. 4. Binding of anti-collagen II Fabs to human cartilage.

Human cartilage was obtained from osteoarthritis patients (Northland Laboratories). The cartilage was first pulverized and stored as a suspension in PBS with protease inhibitors at 4° C. To test for cartilage binding, 2.5 μL of cartilage suspension per data point was added to 97.5 μL of TBST with 3% milk and the mixture rotated at room temperature for one hour. Binding of Fabs to the cartilage was tested using a MultiScreen HTS plate (Millipore) using the vacuum manifold. Briefly, 100 μL of the suspension was added into prewetted MultiScreen plate, and vacuum was applied to settle the cartilage onto the well filter, after which the wells were washed twice with TBST. 2.4 μg of each Fab in 100 μL of PBS was added to the wells and incubated at room temperature for 1 hour. The wells were washed three times with TBST, and anti-kappa-HRP (Southern Biotech) was added onto the wells. After one hour incubation, the wells were washed in PBST, the BM Chemiluminescence ELISA Substrate (Roche Applied Science) was added, and the resultant suspension of cartilage fragments was transferred to a black-well ELISA plate for luminescence detection. All 13 Fabs exhibited cartilage binding (FIG. 4).

EXAMPLE 4 mAb Affinities to Col II

ELISA

EC50 values were obtained for select Fabs using ELISA assay as described above. In the assays, 100 microliters of each Fab was added in a concentration range between 10 ng/ml-10 μg/ml onto the wells. The EC50 values are shown in Table 6.

Biacore

Biacore binding kinetics was performed using standard methods against human and rat collagen II (Table 6b).

TABLE 6a

| Fab | EC50 (ng/ml) |
|---|---|
| 551-3 | 113.5 |
| 323-G1 | 123.1 |
| 169-31 | 113.1 |

TABLE 6b

| | human collagen II | | | rat collagen II | | |
|---|---|---|---|---|---|---|
| Fab | $K_a \times 10^5$ | $K_d \times 10^{-3}$ | $K_D$ (nmol) | $K_a \times 10^5$ | $K_d \times 10^{-3}$ | $K_D$ (nmol) |
| 323-G1 | 1.84 | 1.08 | 6 | 2.94 | 1.39 | 5 |
| 169-31 | 0.97 | 5 | 50 | 1.05 | 7.89 | 75 |
| CNTO 4234 | n.a. | n.a. | >1000 | n.a. | n.a. | >1000 |

EXAMPLE 5

Anti-Collagen II mAbs are Retained in the Joints In Vivo

Two anti-collagen II Fabs (323-G1 (CNTO 3631) and 169-31 (CNTO 4093) and a control mAb (CNTO 4234) that did not bind to extracellular matrix components were iodinated and injected into the knees of menisectomized rats to evaluate the effect of mAb binding to collagen on joint residence time. Fabs were radiolabeled using $Na^{125}I$ (Perkin Elmer) and Iodo-GEN tubes (Pierce). Free iodine was removed using PD-10 desalting columns (GE Healthcare) and the Fabs were concentrated to 2.2 mg/mL using Amicon Ultra centrifugal filter devices (Millipore; 10,000 MWCO). After iodination, the Fabs were tested for binding of collagen II, and no significant impairment due to iodination was observed.

Figure 5:
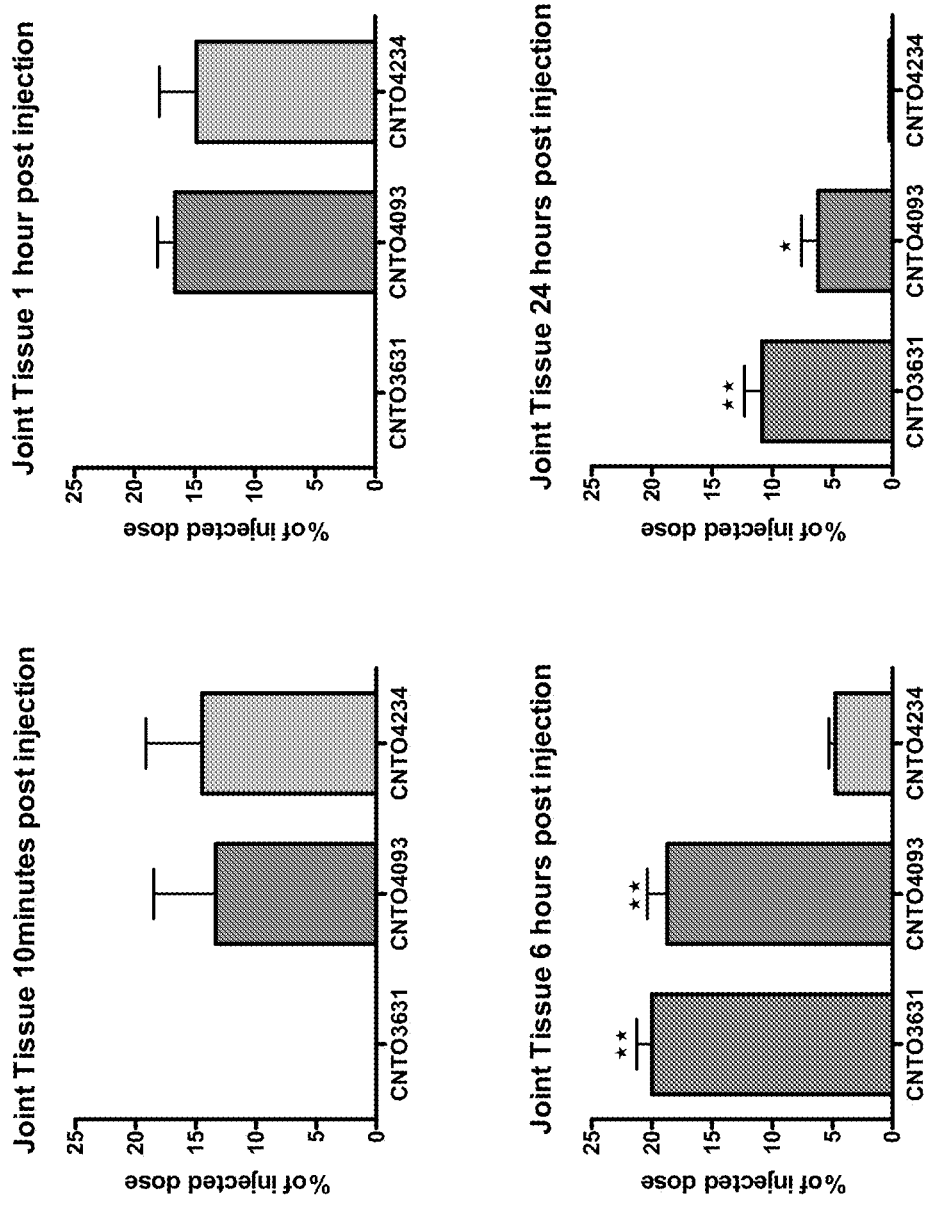
FIG. 5. Retention of anti-collagen II Fabs in osteoarthritic joints. * $P<0.05$, ** $P<0.01$; comparison to control CNTO 4234. The counts at 10 min and 1 hour post injection for CNTO 3631 were too high to read.
Figure 6:
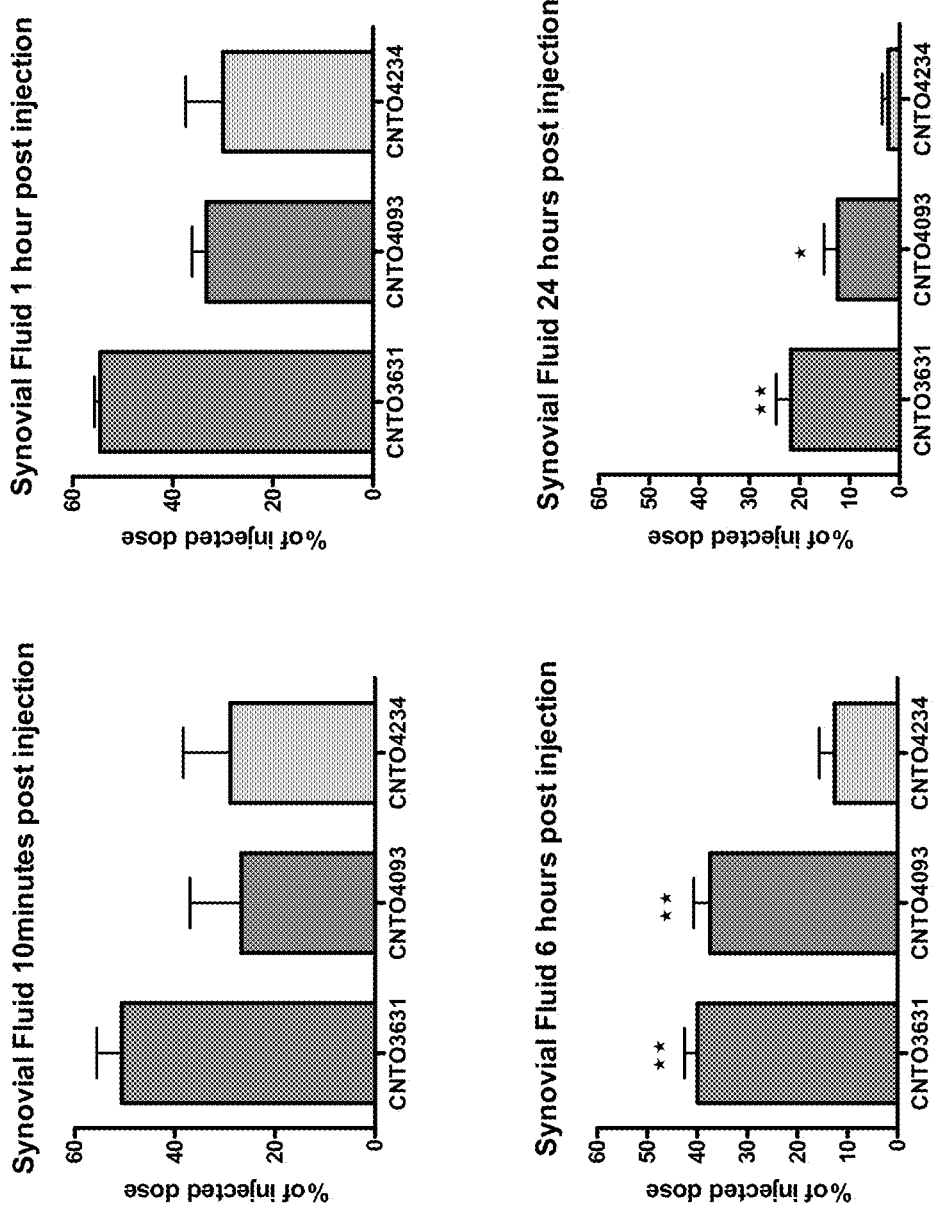
FIG. 6. Retention of anti-collagen II Fabs in osteoarthritic synovial fluid. * $P<0.05$; ** $P<0.01$; comparison to control CNTO 4234.

32 male Sprague-Dawley rats underwent meniscus transection on the right and left hind limb. The rats were anesthetized with isoflurane anesthesia 2-4%, and the medial collateral ligament was transected and the meniscus cut to simulate a tear injury. Joint damage resembling osteoarthritis developed over the next three weeks. Twenty-one days after surgery, intra-articular injections of $^{125}I$-labeled Fabs were performed. Animals received 11 μg of test article through 5 μl intra-articular injections into the right and left knee joint. Animals were euthanized at four time points (10 min, 1 hr, 6 hr and 24 hrs post-injection) and synovial fluid lavage and the knee joints were collected from bot knees. Radioactivity was measured from each sample. The counts per minute (cpm) were compared to the values of the non-injected dose of each respective Fab to calculate the % retention (e.g. as percent of injected dose). 323-G1 (CNTO 3631) and 169-31 (CNTO 4093) were retained both in the knee joint (FIG. 5) and synovial fluid (FIG. 6) longer than the control antibody. Approximately 60% and 32% of Fab 323-G1 and 60% and 18% of Fab 169-31 were retained in the knee (combined joint and synovial retention) after 6 and 24 hours post injection, respectively. The control Fab was retained at 17% and 5%. Thus, the antibodies of the invention exhibited increased joint retention due to their binding to a resident joint protein.

We claim:

1. An isolated polynucleotide encoding an antibody heavy chain variable region comprising the amino acid sequence shown in SEQ ID NO: 64, 66 or 68.

2. An isolated polynucleotide encoding an antibody light chain variable region comprising the amino acid sequence shown in SEQ ID NO: 75 or 76.

3. A vector comprising at least one polynucleotide of claim 1 or 2.

4. An isolated host cell comprising the vector of claim 3.

5. A method of making an antibody that binds human collagen II, comprising culturing the host cell of claim 4 and recovering the antibody produced by the host cell.

* * * * *

SEQUENCE LISTING

<160> NUMBER OF SEQ ID NOS: 80

<210> SEQ ID NO 1
<211> LENGTH: 122
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Ile Tyr Gly Glu Leu Asp Phe Trp Gly Gln Gly
            100                 105                 110

Thr Leu Val Thr Val Ser Ser Ala Ser Thr
        115                 120

<210> SEQ ID NO 2
<211> LENGTH: 122
<212> TYPE: PRT
<213> ORGANISM: Homo sapiens

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Asp Gly Ile Tyr Gly Glu Leu Asp Phe Trp Gly Gln Gly
            100                 105                 110

Thr Leu Val Thr Val Ser Ser Ala Ser Thr
        115                 120

<210> SEQ ID NO 3
<211> LENGTH: 122
<212> TYPE: PRT
<213> ORGANISM: Homo sapiens

<400> SEQUENCE: 3

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Asp Gly Ile Tyr Gly Glu Leu Asp Phe Trp Gly Gln Gly
                100                 105                 110

Thr Leu Val Thr Val Ser Ser Ala Ser Thr
            115                 120

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
                100                 105

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
                100                 105

<210> SEQ ID NO 6

-continued

```
<211> LENGTH: 108
<212> TYPE: PRT
<213> ORGANISM: Homo sapiens

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 7
<211> LENGTH: 115
<212> TYPE: PRT
<213> ORGANISM: Homo sapiens

<400> SEQUENCE: 7

Gln Ala Asp Ile Val Met Thr Gln Ser Pro Asp Ser Leu Ala Val Ser
1               5                   10                  15

Leu Gly Glu Arg Ala Thr Ile Asn Cys Lys Ser Ser Gln Ser Val Leu
            20                  25                  30

Tyr Ser Ser Asn Asn Lys Asn Tyr Leu Ala Trp Tyr Gln Gln Lys Pro
        35                  40                  45

Gly Gln Pro Pro Lys Leu Leu Ile Tyr Trp Ala Ser Thr Arg Glu Ser
50                  55                  60

Gly Val Pro Asp Arg Phe Ser Gly Ser Gly Ser Gly Thr Asp Phe Thr
65                  70                  75                  80

Leu Thr Ile Ser Ser Leu Gln Ala Glu Asp Val Ala Val Tyr Tyr Cys
                85                  90                  95

Gln Gln Tyr Ser Thr Pro Leu Thr Phe Gly Gln Gly Thr Lys Val
            100                 105                 110

Glu Ile Lys
        115

<210> SEQ ID NO 8
<211> LENGTH: 5
<212> TYPE: PRT
<213> ORGANISM: Artificial
<220> FEATURE:
<223> OTHER INFORMATION: HCDR1 of collagen II binding Fab

<400> SEQUENCE: 8

Ser Tyr Gly Ile Ser
1               5

<210> SEQ ID NO 9
<211> LENGTH: 5
<212> TYPE: PRT
<213> ORGANISM: Artificial
<220> FEATURE:
<223> OTHER INFORMATION: HCDR1 of collagen II binding Fab
```

```
<400> SEQUENCE: 9

Ser Tyr Ala Ile Ser
1               5

<210> SEQ ID NO 10
<211> LENGTH: 5
<212> TYPE: PRT
<213> ORGANISM: Artificial
<220> FEATURE:
<223> OTHER INFORMATION: HCDR1 of collagen II binding Fab

<400> SEQUENCE: 10

Ser Tyr Trp Met His
1               5

<210> SEQ ID NO 11
<211> LENGTH: 5
<212> TYPE: PRT
<213> ORGANISM: Artificial
<220> FEATURE:
<223> OTHER INFORMATION: HCDR1 of collagen II binding Fab

<400> SEQUENCE: 11

Asp Tyr Trp Met Ser
1               5

<210> SEQ ID NO 12
<211> LENGTH: 5
<212> TYPE: PRT
<213> ORGANISM: Artificial
<220> FEATURE:
<223> OTHER INFORMATION: HCDR1 of collagen II binding Fab

<400> SEQUENCE: 12

Ser Tyr Ala Met Ser
1               5

<210> SEQ ID NO 13
<211> LENGTH: 5
<212> TYPE: PRT
<213> ORGANISM: Artificial
<220> FEATURE:
<223> OTHER INFORMATION: HCDR1 of collagen II binding Fab

<400> SEQUENCE: 13

Ser Tyr Trp Ile Gly
1               5

<210> SEQ ID NO 14
<211> LENGTH: 17
<212> TYPE: PRT
<213> ORGANISM: Artificial
<220> FEATURE:
<223> OTHER INFORMATION: HCDR1 of collagen II binding Fab

<400> SEQUENCE: 14

Gly Ile Ile Pro Tyr Phe Gly Thr Ala Asn Tyr Ala Gln Lys Phe Gln
1               5                   10                  15

Gly

<210> SEQ ID NO 15
<211> LENGTH: 17
<212> TYPE: PRT
<213> ORGANISM: Artificial
<220> FEATURE:
```

```
<223> OTHER INFORMATION: HCDR2 of collagen II binding Fab

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 17
<212> TYPE: PRT
<213> ORGANISM: Artificial
<220> FEATURE:
<223> OTHER INFORMATION: HCDR2 of collagen II binding Fab

<400> SEQUENCE: 16

Ala Ile Ser Gly Ser Gly Gly Ser Thr Tyr Tyr Ala Asp Ser Val Lys
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: HCDR2 of collagen II binding Fab

<400> SEQUENCE: 17

Gly Ile Trp Gly Ser Gly Ser Ser Thr Tyr Tyr Ala Asp Ser Val Lys
1               5                   10                  15

Gly

<210> SEQ ID NO 18
<211> LENGTH: 17
<212> TYPE: PRT
<213> ORGANISM: Artificial
<220> FEATURE:
<223> OTHER INFORMATION: HCDR2 of collagen II binding Fab

<400> SEQUENCE: 18

Ala Ile Arg Tyr Asp Gly Ser Ser Lys Tyr Tyr Ala Asp Ser Val Lys
1               5                   10                  15

Gly

<210> SEQ ID NO 19
<211> LENGTH: 17
<212> TYPE: PRT
<213> ORGANISM: Artificial
<220> FEATURE:
<223> OTHER INFORMATION: HCDR2 of collagen II binding Fab

<400> SEQUENCE: 19

Ile Ile Tyr Pro Gly Asp Ser Asp Thr Arg Tyr Ser Pro Ser Phe Gln
1               5                   10                  15

Gly

<210> SEQ ID NO 20
<211> LENGTH: 7
<212> TYPE: PRT
<213> ORGANISM: Artificial
<220> FEATURE:
<223> OTHER INFORMATION: HCDR3 of collagen II binding Fab

<400> SEQUENCE: 20
```

Pro Thr Asn Val Leu Asp Tyr
1               5

<210> SEQ ID NO 21
<211> LENGTH: 6
<212> TYPE: PRT
<213> ORGANISM: Artificial
<220> FEATURE:
<223> OTHER INFORMATION: HCDR3 of collagen II binding Fab

<400> SEQUENCE: 21

His Trp Arg Leu Asn Tyr
1               5

<210> SEQ ID NO 22
<211> LENGTH: 14
<212> TYPE: PRT
<213> ORGANISM: Artificial
<220> FEATURE:
<223> OTHER INFORMATION: HCDR3 of collagen II binding Fab

<400> SEQUENCE: 22

Asp Pro Asn Gly Asn Ile Val Leu Ser Glu Tyr Phe Asp Tyr
1               5                   10

<210> SEQ ID NO 23
<211> LENGTH: 13
<212> TYPE: PRT
<213> ORGANISM: Artificial
<220> FEATURE:
<223> OTHER INFORMATION: HCDR3 of collagen II binding Fab

<400> SEQUENCE: 23

Glu Gly Pro Ala Ser Trp Asp Asn Trp Ala Leu Asp Tyr
1               5                   10

<210> SEQ ID NO 24
<211> LENGTH: 7
<212> TYPE: PRT
<213> ORGANISM: Artificial
<220> FEATURE:
<223> OTHER INFORMATION: HCDR3 of collagen II binding Fab

<400> SEQUENCE: 24

Arg Leu Gly Leu Phe Asp Tyr
1               5

<210> SEQ ID NO 25
<211> LENGTH: 12
<212> TYPE: PRT
<213> ORGANISM: Artificial
<220> FEATURE:
<223> OTHER INFORMATION: HCDR3 of collagen II binding Fab

<400> SEQUENCE: 25

Asp Gly Tyr Asp Ile Val Leu Gly Ile Phe Asp Tyr
1               5                   10

<210> SEQ ID NO 26
<211> LENGTH: 10
<212> TYPE: PRT
<213> ORGANISM: Artificial
<220> FEATURE:
<223> OTHER INFORMATION: HCDR3 of collagen II binding Fab

<400> SEQUENCE: 26

Asn Ile Val Gly Asp Tyr Leu Leu Asp Tyr

```
<210> SEQ ID NO 27
<211> LENGTH: 7
<212> TYPE: PRT
<213> ORGANISM: Artificial
<220> FEATURE:
<223> OTHER INFORMATION: HCDR3 of collagen II binding Fab

<400> SEQUENCE: 27

Thr Ser Pro Ser Phe Asp Tyr
1               5

<210> SEQ ID NO 28
<211> LENGTH: 8
<212> TYPE: PRT
<213> ORGANISM: Artificial
<220> FEATURE:
<223> OTHER INFORMATION: HCDR3 of collagen II binding Fab

<400> SEQUENCE: 28

His Leu Tyr Tyr Met Leu Asp Tyr
1               5

<210> SEQ ID NO 29
<211> LENGTH: 12
<212> TYPE: PRT
<213> ORGANISM: Artificial
<220> FEATURE:
<223> OTHER INFORMATION: HCDR3 of collagen II binding Fab

<400> SEQUENCE: 29

Tyr Leu Arg Trp Gly Ser Tyr Gly Ile Leu Asp Tyr
1               5                   10

<210> SEQ ID NO 30
<211> LENGTH: 10
<212> TYPE: PRT
<213> ORGANISM: Artificial
<220> FEATURE:
<223> OTHER INFORMATION: HCDR3 of collagen II binding Fab

<400> SEQUENCE: 30

His Trp Gly Arg Gly Gly Asp Leu Asp Tyr
1               5                   10

<210> SEQ ID NO 31
<211> LENGTH: 7
<212> TYPE: PRT
<213> ORGANISM: Artificial
<220> FEATURE:
<223> OTHER INFORMATION: HCDR3 of collagen II binding Fab

<400> SEQUENCE: 31

Asn Leu Lys Ile Leu Asp Tyr
1               5

<210> SEQ ID NO 32
<211> LENGTH: 8
<212> TYPE: PRT
<213> ORGANISM: Artificial
<220> FEATURE:
<223> OTHER INFORMATION: HCDR3 of collagen II binding Fab

<400> SEQUENCE: 32

Gly Leu Phe Trp Phe Phe Asp Tyr
1               5
```

```
<210> SEQ ID NO 33
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 33

Arg Ala Ser Gln Ser Val Arg Lys Phe Leu Ala
1               5                   10

<210> SEQ ID NO 34
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 34

Arg Ala Ser Gln Ser Val Ser Ser Tyr Leu Ala
1               5                   10

<210> SEQ ID NO 35
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 35

Arg Ala Ser Gln Ser Val Arg Asp Phe Leu Ala
1               5                   10

<210> SEQ ID NO 36
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 36

Arg Ala Ser Gln Ser Val Ser Asp Trp Leu Ala
1               5                   10

<210> SEQ ID NO 37
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 37

Arg Ala Ser Gln Ser Val Asp Ser Ala Leu Ala
1               5                   10

<210> SEQ ID NO 38
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 38

Arg Ala Ser Gln Ser Val Asp Asp Trp Leu Ala
1               5                   10
```

<210> SEQ ID NO 39
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 39

Arg Ala Ser Gln Ser Val Ala Asp Trp Leu Ala
1               5                   10

<210> SEQ ID NO 40
<211> LENGTH: 17
<212> TYPE: PRT
<213> ORGANISM: Artificial
<220> FEATURE:
<223> OTHER INFORMATION: LCDR1 of collagen II binding Fab

<400> SEQUENCE: 40

Lys Ser Ser Gln Ser Val Leu Tyr Ser Ser Asn Asn Lys Asn Tyr Leu
1               5                   10                  15

Ala

<210> SEQ ID NO 41
<211> LENGTH: 11
<212> TYPE: PRT
<213> ORGANISM: Artificial
<220> FEATURE:
<223> OTHER INFORMATION: LCDR1 of collagen II binding Fab

<400> SEQUENCE: 41

Arg Ala Ser Gln Ser Val Asp Ser Trp Leu Ala
1               5                   10

<210> SEQ ID NO 42
<211> LENGTH: 7
<212> TYPE: PRT
<213> ORGANISM: Artificial
<220> FEATURE:
<223> OTHER INFORMATION: LCDR2 of collagen II binding Fab

<400> SEQUENCE: 42

Asp Ala Ser Asn Arg Ala Thr
1               5

<210> SEQ ID NO 43
<211> LENGTH: 7
<212> TYPE: PRT
<213> ORGANISM: Artificial
<220> FEATURE:
<223> OTHER INFORMATION: LCDR2 of collagen II binding Fab

<400> SEQUENCE: 43

Gly Ala Ser Asn Arg Ala Thr
1               5

<210> SEQ ID NO 44
<211> LENGTH: 7
<212> TYPE: PRT
<213> ORGANISM: Artificial
<220> FEATURE:
<223> OTHER INFORMATION: LCDR2 of collagen II binding Fab

<400> SEQUENCE: 44

Tyr Ala Ser Asn Arg Ala Thr
1               5

```
<210> SEQ ID NO 45
<211> LENGTH: 7
<212> TYPE: PRT
<213> ORGANISM: Artificial
<220> FEATURE:
<223> OTHER INFORMATION: LCDR2 of collagen II binding Fab

<400> SEQUENCE: 45

Trp Ala Ser Thr Arg Glu Ser
1               5

<210> SEQ ID NO 46
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 46

Gln Gln Ser Asn Asn Trp Pro Phe Thr
1               5

<210> SEQ ID NO 47
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 47

Gln Gln Arg Ser Asn Trp Pro Leu Thr
1               5

<210> SEQ ID NO 48
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 48

Gln Gln Arg Gly Ser Ala Pro Leu Thr
1               5

<210> SEQ ID NO 49
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 49

Gln Gln Ser Ser Thr Ala Pro Ile Thr
1               5

<210> SEQ ID NO 50
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 50

Gln Gln Tyr Asp Arg Trp Pro Leu Thr
1               5
```

```
<210> SEQ ID NO 51
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 51

Gln Gln Gly Asp Thr Ala Pro Ile Thr
1               5

<210> SEQ ID NO 52
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 52

Gln Gln Gly Phe His Trp Pro Phe Thr
1               5

<210> SEQ ID NO 53
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 53

Gln Gln Tyr Asp Gly Trp Pro Ile Thr
1               5

<210> SEQ ID NO 54
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 54

Gln Gln Tyr Tyr Ser Thr Pro Leu Thr
1               5

<210> SEQ ID NO 55
<211> LENGTH: 9
<212> TYPE: PRT
<213> ORGANISM: Artificial
<220> FEATURE:
<223> OTHER INFORMATION: LCDR3 of collagen II binding Fab

<400> SEQUENCE: 55

Gln Gln Phe Asp Thr Trp Pro Ile Thr
1               5

<210> SEQ ID NO 56
<211> LENGTH: 116
<212> TYPE: PRT
<213> ORGANISM: Artificial
<220> FEATURE:
<223> OTHER INFORMATION: VH of collagen II binding Fab

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
```

```
                        20                  25                  30
Gly Ile Ser Trp Val Arg Gln Ala Pro Gly Gln Gly Leu Glu Trp Met
            35                  40                  45
Gly Gly Ile Ile Pro Tyr Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Pro Thr Asn Val Leu Asp Tyr Trp Gly Gln Gly Thr Leu Val
            100                 105                 110
Thr Val Ser Ser
        115

<210> SEQ ID NO 57
<211> LENGTH: 115
<212> TYPE: PRT
<213> ORGANISM: Artificial
<220> FEATURE:
<223> OTHER INFORMATION: VH of collagen II binding Fab

<400> SEQUENCE: 57

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg His Trp Arg Leu Asn Tyr Trp Gly Gln Gly Thr Leu Val Thr
            100                 105                 110
Val Ser Ser
        115

<210> SEQ ID NO 58
<211> LENGTH: 123
<212> TYPE: PRT
<213> ORGANISM: Artificial
<220> FEATURE:
<223> OTHER INFORMATION: VH of collagen II binding Fab

<400> SEQUENCE: 58

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
    50                  55                  60
Gln Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                 85                  90                  95

Ala Arg Asp Pro Asn Gly Asn Ile Val Leu Ser Glu Tyr Phe Asp Tyr
            100                 105                 110

Trp Gly Gln Gly Thr Leu Val Thr Val Ser Ser
        115                 120
```

<210> SEQ ID NO 59
<211> LENGTH: 122
<212> TYPE: PRT
<213> ORGANISM: Artificial
<220> FEATURE:
<223> OTHER INFORMATION: VH of collagen II binding Fab

<400> SEQUENCE: 59

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Pro Ala Ser Trp Asp Asn Trp Ala Leu Asp Tyr Trp
            100                 105                 110

Gly Gln Gly Thr Leu Val Thr Val Ser Ser
        115                 120
```

<210> SEQ ID NO 60
<211> LENGTH: 116
<212> TYPE: PRT
<213> ORGANISM: Artificial
<220> FEATURE:
<223> OTHER INFORMATION: VH of collagen II binding Fab

<400> SEQUENCE: 60

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Leu Gly Leu Phe Asp Tyr Trp Gly Gln Gly Thr Leu Val
            100                 105                 110

Thr Val Ser Ser
        115
```

<210> SEQ ID NO 61

<211> LENGTH: 121
<212> TYPE: PRT
<213> ORGANISM: Artificial
<220> FEATURE:
<223> OTHER INFORMATION: VH of collagen II binding Fab

<400> SEQUENCE: 61

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Ile Val Leu Gly Ile Phe Asp Tyr Trp Gly
            100                 105                 110

Gln Gly Thr Leu Val Thr Val Ser Ser
        115                 120

<210> SEQ ID NO 62
<211> LENGTH: 119
<212> TYPE: PRT
<213> ORGANISM: Artificial
<220> FEATURE:
<223> OTHER INFORMATION: VH of collagen II binding Fab

<400> SEQUENCE: 62

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Ile Val Gly Asp Tyr Leu Leu Asp Tyr Trp Gly Gln Gly
            100                 105                 110

Thr Leu Val Thr Val Ser Ser
        115

<210> SEQ ID NO 63
<211> LENGTH: 116
<212> TYPE: PRT
<213> ORGANISM: Artificial
<220> FEATURE:
<223> OTHER INFORMATION: VH of collagen II binding Fab

<400> SEQUENCE: 63

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Ser Pro Ser Phe Asp Tyr Trp Gly Gln Gly Thr Leu Val
            100                 105                 110

Thr Val Ser Ser
        115

<210> SEQ ID NO 64
<211> LENGTH: 117
<212> TYPE: PRT
<213> ORGANISM: Artificial
<220> FEATURE:
<223> OTHER INFORMATION: VH of collagen II binding Fab

<400> SEQUENCE: 64

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Leu Tyr Tyr Met Leu Asp Tyr Trp Gly Gln Gly Thr Leu
            100                 105                 110

Val Thr Val Ser Ser
        115

<210> SEQ ID NO 65
<211> LENGTH: 121
<212> TYPE: PRT
<213> ORGANISM: Artificial
<220> FEATURE:
<223> OTHER INFORMATION: VH of collagen II binding Fab

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Tyr Leu Arg Trp Gly Ser Tyr Gly Ile Leu Asp Tyr Trp Gly
            100                 105                 110

Gln Gly Thr Leu Val Thr Val Ser Ser
        115                 120

<210> SEQ ID NO 66
<211> LENGTH: 119
<212> TYPE: PRT
<213> ORGANISM: Artificial
<220> FEATURE:
<223> OTHER INFORMATION: VH of collagen II binding Fab

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Ser Gly Ile Trp Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Trp Gly Arg Gly Gly Asp Leu Asp Tyr Trp Gly Gln Gly
            100                 105                 110

Thr Leu Val Thr Val Ser Ser
        115

<210> SEQ ID NO 67
<211> LENGTH: 116
<212> TYPE: PRT
<213> ORGANISM: Artificial
<220> FEATURE:
<223> OTHER INFORMATION: VH of collagen II binding Fab

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Arg Tyr Asp Gly Ser Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Lys Ile Leu Asp Tyr Trp Gly Gln Gly Thr Leu Val
            100                 105                 110

Thr Val Ser Ser
        115
```

-continued

```
<210> SEQ ID NO 68
<211> LENGTH: 117
<212> TYPE: PRT
<213> ORGANISM: Artificial
<220> FEATURE:
<223> OTHER INFORMATION: VH of collagen II binding Fab

<400> SEQUENCE: 68
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Leu Phe Trp Phe Phe Asp Tyr Trp Gly Gln Gly Thr Leu
            100                 105                 110

Val Thr Val Ser Ser
        115

```
<210> SEQ ID NO 69
<211> LENGTH: 107
<212> TYPE: PRT
<213> ORGANISM: Artificial
<220> FEATURE:
<223> OTHER INFORMATION: VL of collagen II binding Fab

<400> SEQUENCE: 69
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Lys Phe
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Asn Trp Pro Phe
                85                  90                  95

Thr Phe Gly Gln Gly Thr Lys Val Glu Ile Lys
            100                 105

```
<210> SEQ ID NO 70
<211> LENGTH: 123
<212> TYPE: PRT
<213> ORGANISM: Artificial
<220> FEATURE:
<223> OTHER INFORMATION: VL of collagen II binding Fab

<400> SEQUENCE: 70
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Asn Gly Asn Ile Val Leu Ser Glu Tyr Phe Asp Tyr
                100                 105                 110

Trp Gly Gln Gly Thr Leu Val Thr Val Ser Ser
            115                 120

<210> SEQ ID NO 71
<211> LENGTH: 107
<212> TYPE: PRT
<213> ORGANISM: Artificial
<220> FEATURE:
<223> OTHER INFORMATION: VL of collagen II binding Fab

<400> SEQUENCE: 71

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Trp
            20                  25                  30

Leu Ala Trp Tyr Gln Gln Lys Pro Gly Gln Ala Pro Arg Leu Leu Ile
        35                  40                  45

Tyr Tyr Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Thr Ala Pro Ile
                85                  90                  95

Thr Phe Gly Gln Gly Thr Lys Val Glu Ile Lys
            100                 105

<210> SEQ ID NO 72
<211> LENGTH: 107
<212> TYPE: PRT
<213> ORGANISM: Artificial
<220> FEATURE:
<223> OTHER INFORMATION: VL of collagen II binding Fab

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Ala
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Arg Trp Pro Leu
                85                  90                  95

Thr Phe Gly Gln Gly Thr Lys Val Glu Ile Lys

<210> SEQ ID NO 73
<211> LENGTH: 107
<212> TYPE: PRT
<213> ORGANISM: Artificial
<220> FEATURE:
<223> OTHER INFORMATION: VL of collagen II binding Fab

<400> SEQUENCE: 73

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Asp Trp
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Asp Thr Ala Pro Ile
                85                  90                  95

Thr Phe Gly Gln Gly Thr Lys Val Glu Ile Lys
            100                 105

<210> SEQ ID NO 74
<211> LENGTH: 107
<212> TYPE: PRT
<213> ORGANISM: Artificial
<220> FEATURE:
<223> OTHER INFORMATION: VL of collagen II binding Fab

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Asp Phe
            20                  25                  30

Leu Ala Trp Tyr Gln Gln Lys Pro Gly Gln Ala Pro Arg Leu Leu Ile
        35                  40                  45

Tyr Tyr Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Phe His Trp Pro Phe
                85                  90                  95

Thr Phe Gly Gln Gly Thr Lys Val Glu Ile Lys
            100                 105

<210> SEQ ID NO 75
<211> LENGTH: 107
<212> TYPE: PRT
<213> ORGANISM: Artificial
<220> FEATURE:
<223> OTHER INFORMATION: VL of collagen II binding Fab

<400> SEQUENCE: 75

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ala Asp Trp
            20                  25                  30

```
Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Asp Gly Trp Pro Ile
                85                  90                  95

Thr Phe Gly Gln Gly Thr Lys Val Glu Ile Lys
            100                 105

<210> SEQ ID NO 76
<211> LENGTH: 107
<212> TYPE: PRT
<213> ORGANISM: Artificial
<220> FEATURE:
<223> OTHER INFORMATION: VL of collagen II binding Fab

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asp Ser Trp
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Thr Trp Pro Ile
                85                  90                  95

Thr Phe Gly Gln Gly Thr Lys Val Glu Ile Lys
            100                 105

<210> SEQ ID NO 77
<211> LENGTH: 330
<212> TYPE: PRT
<213> ORGANISM: Homo sapiens

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 78
<211> LENGTH: 327
<212> TYPE: PRT
<213> ORGANISM: Homo sapiens

<400> SEQUENCE: 78

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175
```

```
Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 79
<211> LENGTH: 1487
<212> TYPE: PRT
<213> ORGANISM: Homo sapiens

<400> SEQUENCE: 79

Met Ile Arg Leu Gly Ala Pro Gln Thr Leu Val Leu Leu Thr Leu Leu
1               5                   10                  15

Val Ala Ala Val Leu Arg Cys Gln Gly Gln Asp Val Gln Glu Ala Gly
            20                  25                  30

Ser Cys Val Gln Asp Gly Gln Arg Tyr Asn Asp Lys Asp Val Trp Lys
        35                  40                  45

Pro Glu Pro Cys Arg Ile Cys Val Cys Asp Thr Gly Thr Val Leu Cys
    50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
```

```
            210                 215                 220
Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
            245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
                275                 280                 285

His Arg Gly Tyr Pro Gly Leu Asp Gly Ala Lys Gly Glu Ala Gly Ala
            290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
            355                 360                 365

Gly Ala Pro Gly Ala Lys Gly Glu Ala Gly Pro Thr Gly Ala Arg Gly
            370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
            435                 440                 445

Leu Gly Pro Lys Gly Gln Thr Gly Glu Pro Gly Ile Ala Gly Phe Lys
            450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495

Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
                565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605

Gly Ala Asn Gly Glu Pro Gly Lys Ala Gly Glu Lys Gly Leu Pro Gly
            610                 615                 620

Ala Pro Gly Leu Arg Gly Leu Pro Gly Lys Asp Gly Glu Thr Gly Ala
625                 630                 635                 640
```

```
Ala Gly Pro Pro Gly Pro Ala Gly Pro Ala Gly Glu Arg Gly Glu Gln
                645                 650                 655

Gly Ala Pro Gly Pro Ser Gly Phe Gln Gly Leu Pro Gly Pro Pro Gly
            660                 665                 670

Pro Pro Gly Glu Gly Gly Lys Pro Gly Asp Gln Gly Val Pro Gly Glu
        675                 680                 685

Ala Gly Ala Pro Gly Leu Val Gly Pro Arg Gly Glu Arg Gly Phe Pro
    690                 695                 700

Gly Glu Arg Gly Ser Pro Gly Ala Gln Gly Leu Gln Gly Pro Arg Gly
705                 710                 715                 720

Leu Pro Gly Thr Pro Gly Thr Asp Gly Pro Lys Gly Ala Ser Gly Pro
            725                 730                 735

Ala Gly Pro Pro Gly Ala Gln Gly Pro Pro Gly Leu Gln Gly Met Pro
        740                 745                 750

Gly Glu Arg Gly Ala Ala Gly Ile Ala Gly Pro Lys Gly Asp Arg Gly
    755                 760                 765

Asp Val Gly Glu Lys Gly Pro Glu Gly Ala Pro Gly Lys Asp Gly Gly
    770                 775                 780

Arg Gly Leu Thr Gly Pro Ile Gly Pro Pro Gly Pro Ala Gly Ala Asn
785                 790                 795                 800

Gly Glu Lys Gly Glu Val Gly Pro Pro Gly Pro Ala Gly Ser Ala Gly
            805                 810                 815

Ala Arg Gly Ala Pro Gly Glu Arg Gly Glu Thr Gly Pro Pro Gly Pro
        820                 825                 830

Ala Gly Phe Ala Gly Pro Pro Gly Ala Asp Gly Gln Pro Gly Ala Lys
    835                 840                 845

Gly Glu Gln Gly Glu Ala Gly Gln Lys Gly Asp Ala Gly Ala Pro Gly
    850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
            885                 890                 895

Gly Phe Pro Gly Ala Ala Gly Arg Val Gly Pro Pro Gly Ser Asn Gly
        900                 905                 910

Asn Pro Gly Pro Pro Gly Pro Pro Gly Pro Ser Gly Lys Asp Gly Pro
    915                 920                 925

Lys Gly Ala Arg Gly Asp Ser Gly Pro Pro Gly Arg Ala Gly Glu Pro
    930                 935                 940

Gly Leu Gln Gly Pro Ala Gly Pro Pro Gly Glu Lys Gly Glu Pro Gly
945                 950                 955                 960

Asp Asp Gly Pro Ser Gly Ala Glu Gly Pro Pro Gly Pro Gln Gly Leu
            965                 970                 975

Ala Gly Gln Arg Gly Ile Val Gly Leu Pro Gly Gln Arg Gly Glu Arg
        980                 985                 990

Gly Phe Pro Gly Leu Pro Gly Pro  Ser Gly Glu Pro Gly  Lys Gln Gly
        995                 1000                1005

Ala Pro  Gly Ala Ser Gly Asp  Arg Gly Pro Pro Gly  Pro Val Gly
        1010                1015                1020

Pro Pro  Gly Leu Thr Gly Pro  Ala Gly Glu Pro Gly  Arg Glu Gly
        1025                1030                1035

Ser Pro  Gly Ala Asp Gly Pro  Pro Gly Arg Asp Gly  Ala Ala Gly
        1040                1045                1050
```

```
Val Lys Gly Asp Arg Gly Glu Thr Gly Ala Val Gly Ala Pro Gly
    1055                1060                1065
Ala Pro Gly Pro Pro Gly Ser Pro Gly Pro Ala Gly Pro Thr Gly
    1070                1075                1080
Lys Gln Gly Asp Arg Gly Glu Ala Gly Ala Gln Gly Pro Met Gly
    1085                1090                1095
Pro Ser Gly Pro Ala Gly Ala Arg Gly Ile Gln Gly Pro Gln Gly
    1100                1105                1110
Pro Arg Gly Asp Lys Gly Glu Ala Gly Glu Pro Gly Glu Arg Gly
    1115                1120                1125
Leu Lys Gly His Arg Gly Phe Thr Gly Leu Gln Gly Leu Pro Gly
    1130                1135                1140
Pro Pro Gly Pro Ser Gly Asp Gln Gly Ala Ser Gly Pro Ala Gly
    1145                1150                1155
Pro Ser Gly Pro Arg Gly Pro Pro Gly Pro Val Gly Pro Ser Gly
    1160                1165                1170
Lys Asp Gly Ala Asn Gly Ile Pro Gly Pro Ile Gly Pro Pro Gly
    1175                1180                1185
Pro Arg Gly Arg Ser Gly Glu Thr Gly Pro Ala Gly Pro Pro Gly
    1190                1195                1200
Asn Pro Gly Pro Pro Gly Pro Pro Gly Pro Pro Gly Pro Gly Ile
    1205                1210                1215
Asp Met Ser Ala Phe Ala Gly Leu Gly Pro Arg Glu Lys Gly Pro
    1220                1225                1230
Asp Pro Leu Gln Tyr Met Arg Ala Asp Gln Ala Ala Gly Gly Leu
    1235                1240                1245
Arg Gln His Asp Ala Glu Val Asp Ala Thr Leu Lys Ser Leu Asn
    1250                1255                1260
Asn Gln Ile Glu Ser Ile Arg Ser Pro Glu Gly Ser Arg Lys Asn
    1265                1270                1275
Pro Ala Arg Thr Cys Arg Asp Leu Lys Leu Cys His Pro Glu Trp
    1280                1285                1290
Lys Ser Gly Asp Tyr Trp Ile Asp Pro Asn Gln Gly Cys Thr Leu
    1295                1300                1305
Asp Ala Met Lys Val Phe Cys Asn Met Glu Thr Gly Glu Thr Cys
    1310                1315                1320
Val Tyr Pro Asn Pro Ala Asn Val Pro Lys Lys Asn Trp Trp Ser
    1325                1330                1335
Ser Lys Ser Lys Glu Lys Lys His Ile Trp Phe Gly Glu Thr Ile
    1340                1345                1350
Asn Gly Gly Phe His Phe Ser Tyr Gly Asp Asp Asn Leu Ala Pro
    1355                1360                1365
Asn Thr Ala Asn Val Gln Met Thr Phe Leu Arg Leu Leu Ser Thr
    1370                1375                1380
Glu Gly Ser Gln Asn Ile Thr Tyr His Cys Lys Asn Ser Ile Ala
    1385                1390                1395
Tyr Leu Asp Glu Ala Ala Gly Asn Leu Lys Lys Ala Leu Leu Ile
    1400                1405                1410
Gln Gly Ser Asn Asp Val Glu Ile Arg Ala Glu Gly Asn Ser Arg
    1415                1420                1425
Phe Thr Tyr Thr Ala Leu Lys Asp Gly Cys Thr Lys His Thr Gly
    1430                1435                1440
Lys Trp Gly Lys Thr Val Ile Glu Tyr Arg Ser Gln Lys Thr Ser
```

```
                   1445                1450                1455

Arg Leu Pro Ile Ile Asp Ile Ala Pro Met Asp Ile Gly Gly Pro
        1460                1465                1470

Glu Gln Glu Phe Gly Val Asp Ile Gly Pro Val Cys Phe Leu
        1475                1480                1485

<210> SEQ ID NO 80
<211> LENGTH: 11
<212> TYPE: PRT
<213> ORGANISM: Homo sapiens

<400> SEQUENCE: 80

Ala Cys Asp Glu Gly Lys Asn Arg Ser Tyr Trp
1               5                   10
```